(12) United States Patent
Koll et al.

(10) Patent No.: US 7,022,322 B2
(45) Date of Patent: Apr. 4, 2006

(54) TREATMENT OF CARDIOMYOPATHY BY REMOVAL OF AUTOANTIBODIES

(75) Inventors: Robert Koll, Kirchheim (DE); Jutta Müller-Derlich, Germering (DE); Stephan Felix, Falkensee (DE); Petra Reinke, Berlin (DE); Stefan Brehme, Berlin (DE); Gert Baumann, Berlin (DE); Reiner Spaethe, Stamberg (DE)

(73) Assignee: Edwards Lifesciences Corporation, Irvine, CA (US)

( * ) Notice: Subject to any disclaimer, the term of this patent is extended or adjusted under 35 U.S.C. 154(b) by 142 days.

(21) Appl. No.: 10/299,940

(22) Filed: Nov. 19, 2002

(65) Prior Publication Data
US 2003/0125657 A1    Jul. 3, 2003

Related U.S. Application Data

(63) Continuation of application No. 08/559,262, filed on Nov. 15, 1995, now abandoned.

(51) Int. Cl.
*A61K 39/395* (2006.01)
(52) U.S. Cl. .................. 424/140.1; 424/810; 604/5.01; 604/5.02
(58) Field of Classification Search ............. 424/131.1, 424/140.1, 810; 604/5.01, 5.02
See application file for complete search history.

(56) References Cited
U.S. PATENT DOCUMENTS
4,223,672 A    9/1980   Terman et al.

FOREIGN PATENT DOCUMENTS

| WO | WO 91 17171 A | 11/1991 |
|---|---|---|
| WO | 9220811 | * 11/1992 |
| WO | WO 93 24158 A | 12/1993 |
| WO | WO 95 31727 A | 11/1995 |

OTHER PUBLICATIONS

Borberg et al, Transfusion Science, 15, 409-418, 1994.*
Magnusson et al, Journal of Autoimunnity, 4, 893-905, 1991.*

(Continued)

*Primary Examiner*—David Saunders
(74) *Attorney, Agent, or Firm*—B. Aaron Schulman; Debra D. Condino

(57) ABSTRACT

Immunoapheresis treatment for cardiomyopathy comprises passing the patient's plasma over a column having coupled thereto a specific ligand for human immunoglobulin, thereby removing a significant portion of the immunoglobulin from the patient's plasma, and then reinfusing the plasma to the patient. The invention is the use of a specific ligand for human immunoglobulin in the manufacture of a column having the ligand coupled thereto, the column being useful for immunoapheresis treatment of a patient with cardiomyopathy. The specific ligand binds, and thereby removes, human autoantibodies which are harmful to cardiac tissue such as antibodies against $\beta_1$-adrenergic receptors, ADP-ATP carriers, $\alpha$ and $\beta$ myosin heavy chains, and adenine nucleotide translocators. Immunoapheresis treatment using the column results in improvement of hemodynamic parameters such as mean arterial pressure, mean pulmonary pressure, pumonary capillary wedge pressure, right atrial pressure, cardiac output, cariac index, stroke volume index, and systemic vascular resistance.

5 Claims, 1 Drawing Sheet

OTHER PUBLICATIONS

Figure 1:
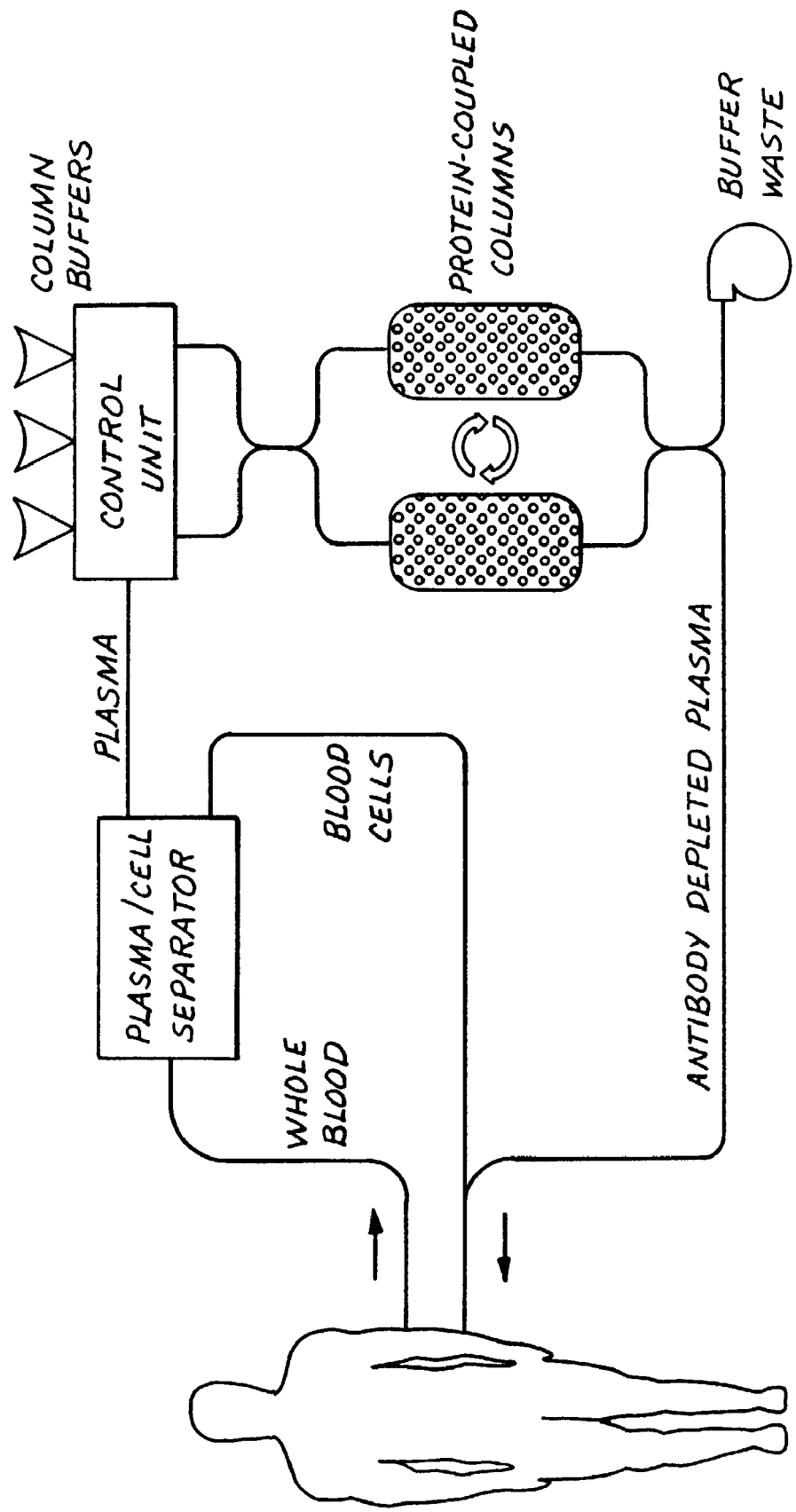

Muller Derlich et al, Immunobiology, vol. 189, Nos. 1-2, p. 237, 1993.*

Schwimmbeck et al. European heart Journal, vol. 11 (Abstr. Suppl. 1), p. 280, 1990.*

Muller et al., "Simultaneous reduction in anti-beta1 adrenoceptor autoantibodies and an improvement in cardiac function during mechanical support . . . ", CIRCULATION, vol. 92, No. 8 Suppl., Oct. 15, 1995.

Muller et al., "Reduction in beta2-receptor autoantibody level in patients with idiopathic dilated cardiomyopathy during mechanical cardiac . . . ", Journal of The American College of Cardiology, No. special issue, Feb. 1995; p. 23A.

Wllukat et al., "Removal of antibodies in dilated cardiomyopathy by immunoadsorption", International Journal of Cardiology, vol. 54, No. 2, May 1996, pp. 191-195.

* cited by examiner

TREATMENT OF CARDIOMYOPATHY BY REMOVAL OF AUTOANTIBODIES

This is a continuation of application Ser. No. 08/559,262, filed Nov. 15, 1995, now abandoned.

Acute and chronic myocarditis is often accompanied by the prevalence of high affinity anti-beta-1 receptor autoantibodies in high titers. Like the catecholamines, these anti-beta-1 receptor autoantibodies activate the beta-adrenergic system. Possible clinical consequences include the destruction of cardial structures with subsequent cardiac insufficiency in the context of a dilatative cardiomyopathy, and persisting arrhythmias as a consequence of the sympathomimetic effect of the anti-beta-1 receptor autoantibodies.

These anti-beta-1 receptor autoantibodies correlate with the severity of dilatative cardiomyopathy. In a clinical trial, the removal of antibodies with the Ig-Therasorb system as described below correlated with the clinical improvement in the patients treated. The clinical results are shown below.

Treatment with the Ig-Therasorb system effects the removal of a high proportion of antibodies of all classes and IgG-subclasses and therefore of antibodies directed against cardiac structures, namely anti-beta-1 receptor autoantibodies. This treatment also removes antibodies of any other specificity against cardiac tissue. It is postulated that removal of these autoantibodies is the basis for the efficacy of Ig-Therasorb treatment of patients with cardiomyopathy.

The treatment schedule foresees an initial series of Ig-Therasorb immunoaphereses within a one or two week period, preferentially three or more Ig-Therasorb immunoaphereses. The initial series of Ig-Therasorb immunoaphereses can be followed by additional immunoaphereses if indicated as determined by autoantibody-monitoring and/or clinical symptoms.

The invention encompasses extracorporeal removal of autoantibodies directed against cardiac structures by removing immunoglobulins of any or all classes and subclasses, for the treatment of cardiomyopathy. Such removal can be accomplished by using any specific ligands for human immunoglobulin coupled to the Therasorb column. Such ligands include polyclonal and monoclonal antihuman immunoglobulin antibodies, fragments of such antibodies (FAB, $FAB_2$) recombinant antibodies or proteins, synthesized peptides, Protein A and Protein G.

The invention also encompasses more specific extracorporeal removal of autoantibodies against cardiac structures, using constructs mimicking the antigen targets of the autoantibodies which are coupled to the Therasorb column. Such antigen-mimicking molecules include anti-idiotypic antibodies (polyclonal or monoclonal), fragments of such antibodies or sythesized peptides, like parts of receptor structures or other chemical substances.

Methods and compositions for the production of sterile and pyrogen-free protein-coupled columns (Ig-Therasorb) are provided in the co-owned U.S. patent application Ser. No. 08/242,215 entitled STERILE AND PYROGEN-FREE COLUMNS COUPLED TO PROTEIN FOR BINDING AND REMOVAL OF SUBSTANCES FROM BLOOD, filed May 13, 1994 now abandoned. This application is herein incorporated by reference, with specific reference to the enabling information contained in the pages as follows:

For production of antibodies and virus inactivation, Example 1, pages 15–19.

For description of pre-columns and working columns, Example 2, pages 19–20.

For sterile purification of antibodies/protein destined to be coupled to the therapeutic column, Example 3, pages 20–25.

For preparation of sterile and pyrogen-free column matrix, Example 4, pages 26–27.

For activation of column matrix material and coupling of protein thereto, Example 5, pages 27–30.

For finishing of final column product, Example 6, page 30.

Immunoapheresis in the clinical setting.

The following will describe experience with clinical immunoapheresis which can be applied to cardiomyopathy patients.

Anti-human immunoglobulin coupled columns were used for the removal of immunoglobulin from the blood of human patients suffering from idiopathic thrombocytopenic purpura (ITP), systemic lupus erythematosus (SLE), vasculitis, and sensitization to HLA. These procedures were part of controlled clinical trials carried out in Europe for the treatment of autoimmune patients whose conditions were refractory to conventional treatments, and patients in need of kidney transplant who had cytotoxic anti-HLA antibodies in their blood.

The apparatus was set up essentially as depicted in FIG. 1.

Briefly, the tubing system of the primary separation system was first filled with sterile 0.9% NaCl. Two anti-human Ig columns (Ig-Therasorb, Baxter, Immunotherapy Division, Europe) were connected with the primary separation system. All tubing connections were made under aseptic conditions.

To remove the preservative solution from the columns, each column was rinsed before its first use with 5 liters sterile 0.9% NaCl solution, at a flow rate of 90–100 ml/min. For each subsequent use, it was sufficient to rinse each column with 2 liters of the sterile solution, at the same flow rate.

Before start of the procedure, the entire system was tested for absence of air bubbles and leaks, correct connections of the solutions, including the anticoagulants, correct installation of the programming of the device, functionality of the automatic clamps, and the safety system.

The appropriate canulae were connected to the left and right cubital veins of the patient. Blood samples were taken. The connection to the blood cell separator was put in place.

Anticoagulation was accomplished with either heparin or citrate (ACD-A or ACD-B). When citrate was the anticoagulant, during the first half of the procedure, the citrate was used at a dilution of 1:22 to 1:18. In the second therapy phase, the dilution utilized was 1:12 to 1:8. Symptoms of hypocalcemia were monitored (paraesthesia in fingers or lips), and the administration of citrate was diminished accordingly. Calcium tablets could be given in cases of frank hypocalcemia.

After the venous puncture and the connection of the tubing system to the patient, the blood cell separator was filled with the patient's blood. The blood flow rate was kept between 50–90 ml/min. When a column with a volume of 100 ml was used, the liquid level was maintained at about 0.8 cm over the Sepharose_in the column. After the stabilization of the separation process, the cell-free plasma was directed through the tubing system over the first column. It was important to keep the flow rate even and to monitor the plasma level over the Sepharose_in the column. A higher plasma level was undesirable, because it would have led to a higher volume burden for the patient, and plasma loss due to plasma retention in the column.

Using a plasma flow rate of up to 40 ml/min, the column was loaded with as much plasma as possible during 15 minutes. Thereafter, the plasma flow was switched to the second column, which was likewise filled with as much plasma as possible in 15 minutes.

During the time of filling of the second column, the plasma in the first column was flushed out using sterile 0.9% NaCl at the plasma flow rate. One column volume of plasma was returned to the patient together with the blood cells which had been removed.

Also during filling of the second column, the first column was regenerated as follows: (1) A further rinse with 50 ml 0.9% NaCl at a flow rate of 100 ml/min; (2) Desorption of the bound immunoglobulin with one column volume of sterile 0.2 M glycine/HCl buffer, pH 2.8. The controller of the device prevented contact between this solution and the patient. The desorbed immunoglobulin was discarded. (3) Neutralization with one column volume of sterile PBS, pH 7.4. Testing of the neutralization using pH indicator paper. (4) Rinsing out of the PBS with at least one column volume of sterile 0.9% Nacl. The column was then ready for the next round of adsorption.

Then, the filling of the columns was again automatically switched. This procedure was repeated as many times as necessary to process the desired volume of plasma. The number of cycles used was chosen by the attending physician, according to the condition and needs of the patient. So far, within the inventors' clinical experience, it has been possible to process up to 3.5 times the extracorporeal volume of a given patient during one column procedure. Moreover, the number of cycles used was not limited by the binding capacity of the columns, but rather by the needs of the individual patient.

Blood samples were taken for analysis of the success of the procedure. Assays for immunoglobulin classes were performed, and tests for anti β-1 receptor autoantibodies were done.

After each procedure, the columns assigned to each patient were cleaned and stored under aseptic conditions at 2–8° C. until the next use for the same patient.

Results: Preliminary results showed that the IgG concentration in the subjects' blood was reduced by at least 70% to over 99% compared to starting concentrations. IgA and IgM levels were reduced by 70% to 90%.

There was no morbidity or mortality associated with the use of the column procedure. Plasma loss was typically low, and no plasma replacement was required.

USE OF IMMUNOAPHERESIS IN TREATMENT OF CARDIOMYOPATHY

Previous studies have shown that sera of patients with dilated cardiomyopathy (DCM) are positive for stimulatory γ-globulin antibodies directed specifically against the $β_1$-adrenergic receptor. These antibodies are extractable by immunoadsorption (IA) which was performed on five consecutive days in nine patients with severe DCM on stable medication. IA caused a decrease of anti $β_1$-adrenergic receptor antibodies from 6.4±1.3 to 1.0±0.5 relative units. During IA, cardiac output increased from 3.7±0.8 to 5.5±1.75 l/min, $p<0.01$. Mean arterial pressure decreased from 76±9.9 to 65±11.2 mmHg, $p<0.05$, mean pulmonary arterial pressure from 27.6±7.7 to 22.0±6.5 mmHg, $p<0.05$, left ventricular filling pressure from 16.8±7.4 to 12.8±4.7 mmHg, $p<0.05$, and systemic vascular resistance decreased from 1465±332 to 949±351 dyn×s×cm$^{-5}$, $p<0.01$.

The cause of injury to the myocardium in DCM is unknown. Consequently, standard treatment is purely symptomatic because it cannot be specifically directed towards aetiology. In recent years evidence accumulated that autoimmunologic mechanisms may play an important role in the initiation and progression of myocardial injury in dilated cardiomyopathy. Several cardiac autoantibodies have been found in dilated cardiomyopathy. Recently it has been shown that autoantibodies directed against the cardiac $β_1$-adrenergic receptors are present in sera from patients with idiopathic dilated cardiomyopathy. These autoantibodies are part of the γ-globulin fraction of patients with DCM and are able to induce a positive chonotrophic effect on neonatal rat heart myocytes in culture. Chronic adrenergic stimulation appears to be an important factor in the pathogenesis of DCM. The activation of the sympathetic nervous system is known to be associated with progressive deterioration of cardiac function and increased mortality in patients with chronic congestive heart failure. To answer the question whether anti $β_1$-adrenergic receptor antibodies with chronotropic activity may play a role in the pathogenesis of dilated cardiomyopathy, IgG was eliminated in 9 patients with severe dilated cardiomyopathy by immunoadsorption (IA).

Nine patients (8 men and 1 woman) with severe chronic congestive heart failure refractory to medical therapy participated in the study. Their ages ranged from 25 to 58, mean age 43.5 years. All patients suffered from dilated cardiomyopathy, New York Heart Association functional class II or IV. The left ventricular ejection fraction was <25% as assessed by left heart catheterization and echocardiography. All patients were on stable medication, including ACE inhibitors, digitalis and diuretics. Because anti β-receptor antibodies are competively displaced by β-blockers patients were additionally treated with β-blockers. β-blocker therapy was started one day prior to IA with esmolol (25 μg/kg/min) intravenously. Esmolol infusion was followed by an oral therapy with metoprolol (mean dose 59.4 mg/day, range 25–100).

Right heart catheterization using a Swan-Ganz thermodilution catheter was performed to determine hemodynamic measurements. The following measurements were made four times a day: systolic and diastolic pulmonary arterial pressure, pulmonary capillary wedge pressure, mean right atrial pressure and cardiac output. The derived hemodynamic variables included: cardiac index, stroke volume index, systemic vascular resistance and pulmonary vascular resistance. Prior to IA the hemodynamic measurements showed a stable baseline of all measured parameters. 2-D echocardiography was used before and after immunoadsorption for the assessment of left ventricular ejection fraction. LV-, RV-, and LA internal dimensions were measured by M-mode echocardiography.

After completion of baseline measurement, the immunglobulin extractions were performed using an immunoadsorber for immunoglobulin, Ig-Therasorb (Baxter Immunotherapy, Munich, Germany). The extracorporeal treatment system consists of conventional plasmapheresis to obtain plasma, and the immunoapheresis system. Immunoapheresis was performed as described above. We used a plasma-separation device (plasma filter OP 05, Diamed) for conventional plasmapheresis. The plasma was separated at a maximal plasma flow rate of 40 ml/min, passed through the immunoadsorption column and was then reinfused. The IA system (ADA, Baxter) consists of two parallel columns. Plasma is passed through one of the columns while the, other is being regenerated. All patients underwent one IA session daily on five consecutive days. In each session IgG plasma levels were decreased by 20–30%. Following the last IA session, all patients received an infusion of approximately 35 g polyclonal IgG to restore serum IgG levels. Anti β-receptor antibodies were determined as previously described (Wallukat, et al. J. Mol. Cell Cardiol. 27:397–406, 1995). The antibody titers were measured after each session.

Results are expressed as mean ±SD. Comparison of measurement before and after immunoadsorption therapy were made with Wilcoxon's-tests and significance was assessed at the $p<0.05$ level.

In all patients, IA procedures were well tolerated and no major complications occurred. Immunoadsorption was effective in reducing $\beta_1$-adrenergic receptor stimulating antibodies in all patients. A decrease of immunoglobulin G (from 11.5 to 1.5 g/l), immunoglobulin A (from 3.3 to 1.4 g/l) and immunoglobulin M (from 1.9 to 0.4 g/l) was detected. Simultaneously, we observed a consistent decrease of $\beta_1$-adrenoreceptor stimulating antibodies (from 6.4±1.3 to 1.0±0.5 Units/l, mean±SD). Heart rate tended to decrease (88.1±23.1 to 84.0±20.8 beats/min, n.s.). Therapy was accomplished by a significant decrease in mean arterial pressure (from 76.0±9.9 to 65.0±11.2 mmHg, $p<0.05$)and mean pulmonary pressure (from 27.6±7.7 to 22.0±6.5 mmHg. $p<0.05$). There was a significant decrease in pulmonary capillary wedge pressure (from 16.8±7.4 to 12.8±4.7 mmHg, $p<0.05$), and right atrial pressure (from 9.1±3.7 to 5.3±3.2 mmHg, $p<0.05$). Cardiac output significantly increased from 3.7±0.8 to 5.5 ±1.8 l/min, $p<0.01$. Cardiac index and stroke volume index increased from 2.0±0.42 to 2.9±0.79 l/min/m, $p<0.01$ and 24.0±7.4 to 35.9±10.3 ml/m$_2$, $p<0.05$, respectively. Resulting from hemodynamic changes mentioned above, systemic vascular resistance decreased progressively (from 1465.4±331.8 to 949.3±351.2 dyn x s x cm$^{-5}$, $p<0.01$ and from 198.9±56.6 to 145.9±69.4 dyn x s x cm$^{-5}$, n.s., respectively). Left ventricular ejection fraction as assessed by echocardiography failed to show a significant improvement (20 to 21.9%). LV-, RV- and LA internal dimensions were unaltered.

In two patients immunoadsorption had to be stopped during therapy because of increased body temperature, which normalized after changing the central-venous catheters.

IA has been successfully used in several autoimmune diseases. It has been shown to remove antiglomerular basement membrane antibodies in Goodpasture's syndrome, antiacetylcholine antibodies in myasthenia gravis and antids DNA antibodies in SLE. Highly sensitized patients awaiting renal transplantation underwent extracorporeal immunoadsorption to remove anti HLA-antibodies (Palmer, et al., Lancet 7:10–12, 1989).

This study reports the hemodynamic effects of immunoadsorption in patients suffering from dilated cardiomyopathy. The decrease of circulating $\beta$-adrenoreceptor autoantibodies was accompanied by an improvement of invasively measured hemodynamic parameters. Removal of other autoimmunereactive antibodies detected in DCM should also be considered. For example, antibodies against the ADP-ATP carrier were able to influence the carrier function and could impair cardiac performance (Schulze).

In summary, immunoadsorption can be an alternative therapeutic principle for acute hemodynamic stabilization in the presence of circulating human antibodies against $\beta_1$ receptors. Immunoadsorption can remove a significant portion of a patient's plasma immunoglobulin. Herein, the term "significant portion" refers to at least 20% of the patient's immunoglobulin. In certain cases, it is desirable to remove up to 80%, and in certain cases more than 80% of the patient's immunoglobulin.

What is claimed is:

1. An immunoapheresis method of treating a patient suffering from dilated cardiomyopathy (DCM) comprising:
   having the patient undergo a plurality of immunoapheresis procedures comprising passing the patient's plasma over a column having coupled thereto a specific ligand selected from the group consisting of a polyclonal or monoclonal anti-human immunoglobulin antibody or a fragment thereof, protein A and protein G, followed by reinfusion of the patient's plasma into the patient, wherein at least 80 percent of the patient's immunoglobulin is removed, and wherein the immunoapheresis procedure is conducted under conditions which promote the binding of the specific ligand to immunocilobulin in the plasma.

2. The method according to claim 1 wherein any autantibodies recognized by the specific ligand are directed against a molecule selected from the group consisting of $\beta_1$-adrenergic receptors, ADP-ATP carriers, $\alpha$ and $\beta$ myosin heavy chains, and adenine nucleotide translocators.

3. The method according to claim 1 wherein the patient is further treated in parallel or subsequent combination with a $\beta$-blocker, intravenous immunoglobulin, or cardiac assist devices.

4. The method according to claim 1 wherein at least three immunoapheresis procedures are performed on the patient within a one or two week period.

5. The method according to claim 1 wherein the immunoapheresis procedure is conducted for at least once a day for five consecutive days.

* * * * *